United States Patent [19]
Phillips et al.

[11] Patent Number: 6,023,981
[45] Date of Patent: *Feb. 15, 2000

[54] SAMPLING BOX

[76] Inventors: Terrance D. Phillips, 617 Chestnut Ct., Aiken, S.C. 29803; Craig Johnson, 100 Midland Rd., Oak Ridge, Tenn. 37831-0895

[*] Notice: This patent issued on a continued prosecution application filed under 37 CFR 1.53(d), and is subject to the twenty year patent term provisions of 35 U.S.C. 154(a)(2).

[21] Appl. No.: 08/675,562

[22] Filed: Jul. 3, 1996

[51] Int. Cl.[7] .................................................. G01N 1/00
[52] U.S. Cl. .......................................................... 73/863.23
[58] Field of Search .......................... 73/863.23, 863.25, 73/863.83, 863.03, 864.34, 864.81, 863.31; 250/288, 440.11, 441.11, 442.11, 443.11, 339.11, 360.1, 379–381; 55/270

[56] References Cited

U.S. PATENT DOCUMENTS

| | | |
|---|---|---|
| 3,252,323 | 5/1966 | Torgenson . |
| 3,362,141 | 1/1968 | Royster, Jr. et al. .................. 73/863.23 |
| 3,593,503 | 7/1971 | Andrews . |
| 3,686,835 | 8/1972 | Strange et al. . |
| 3,841,145 | 10/1974 | Boubel . |
| 3,957,469 | 5/1976 | Nebash . |
| 4,155,247 | 5/1979 | Kaczmarek et al. .................. 73/863.23 |
| 4,382,808 | 5/1983 | Van Wormer, Jr. et al. . |
| 4,426,214 | 1/1984 | Vandrish ............................... 73/863.25 |
| 4,771,642 | 9/1988 | Parth et al. . |
| 5,384,095 | 1/1995 | Golz et al. . |
| 5,404,762 | 4/1995 | Rodgers et al. ....................... 73/863.25 |

*Primary Examiner*—Robert Raevis
*Attorney, Agent, or Firm*—Nexsen Pruet Jacobs & Pollard, LLP

[57] ABSTRACT

An air sampling box that uses a slidable filter tray and a removable filter cartridge to allow for the easy replacement of a filter which catches radioactive particles is disclosed.

9 Claims, 5 Drawing Sheets

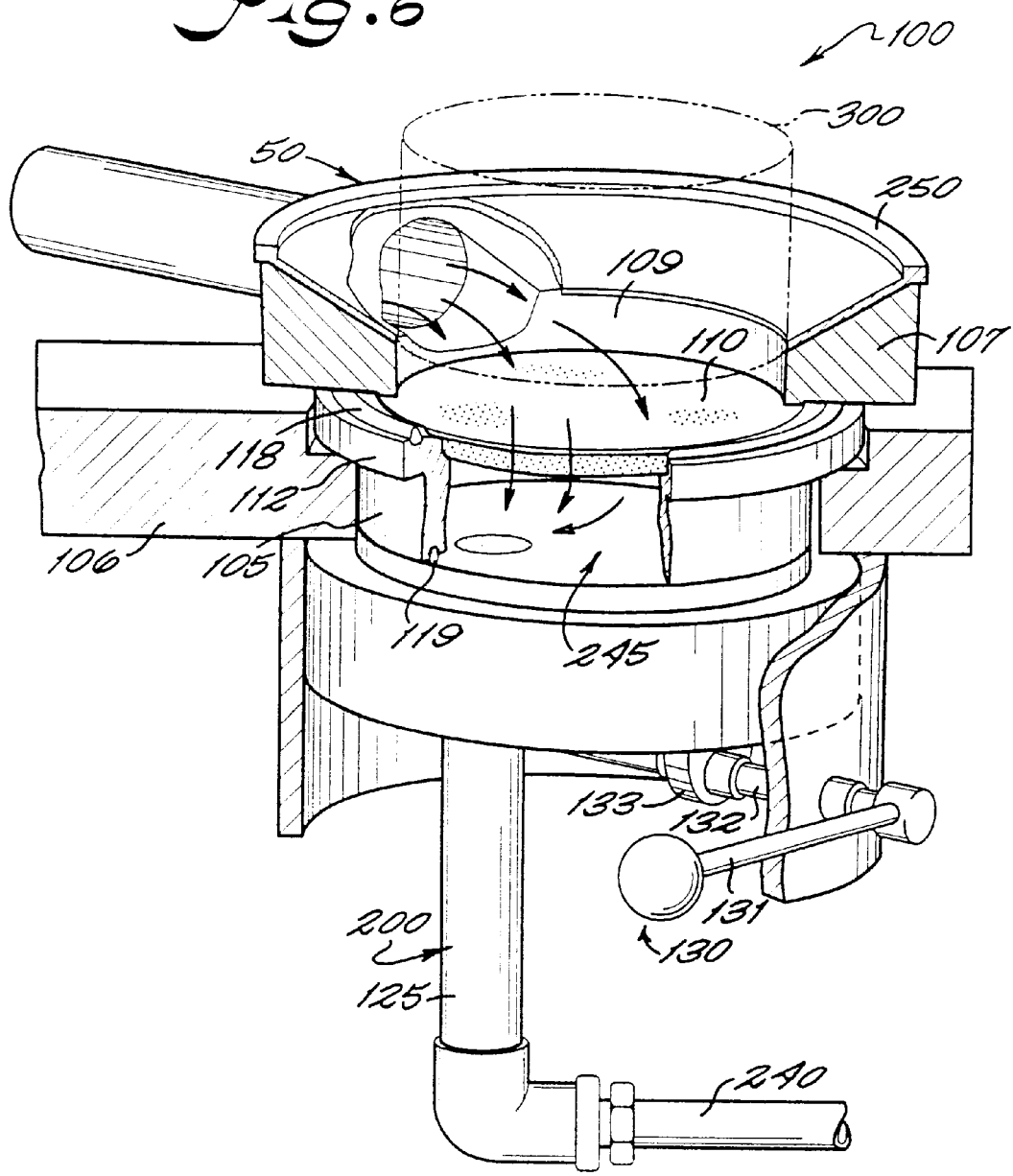

SAMPLING BOX

GOVERNMENT RIGHTS

The United States Government has rights in this invention pursuant to Contract No. DE-AC09-89SR18035 between the United States Department of Energy and Westinghouse Savannah River Company.

DESCRIPTION OF THE PRIOR ART

Radioactive waste storage facilities need to assure that they do not release undue amounts of radioactive particles to the atmosphere through their waste storage ventilation stacks. Accordingly, it has been known to draw a nominal 3 cfm air sample from the stack and send it to a sampling box containing a filter, typically, a 76 mm (diameter) piece of filter paper. Minimally, in accordance with government regulations, the filter papers are collected and measured for radioactive build up at least once a week. The analysis of the radioactive particles collected becomes record data. In addition, it is possible to provide the sampling box with a continuous air monitor (CAM) that continuously measures the amount of radioactive particles trapped within the filter paper by placing a radiation detector slightly above the filter paper. The CAM send its signal to the operator.

The frequency with which the filter paper needs to be replaced, coupled with the continuous desire to have unskilled labor be capable of carrying out more day-to-day tasks, has led to the need for simple methods by which the filter paper can be At replaced. One attempt at achieving this goal is shown in U.S. Pat. No. 5,404,762 to Rodgers et al. Rodgers integrally mounts his filter in a replaceable filter cartridge that is merely dropped into a filter drawer. To replace the filter, one opens the filter drawer, removes the old filter cartridge, drops in a new one, and closes the drawer. Furthermore, by use of a cover plate, Rodgers attempts to assure that no part of the filter cartridge other than the filter becomes contaminated with radioactive materials.

We have determined, however, that Rodgers' device has various flaws in its design. In particular, Rodgers does not have an isolated radioactive testing chamber or a filter hold-down, is only designed for CAM applications (unless his CAM device is shut off), and requires a precise fit between components to assure the unit remains sealed. Furthermore, Rodgers' filter cartridge, itself, is fairly complex and large and his device has 90° bends that reduce efficiency and do not assure that radioactive particles will be deposited in (on) the center of the filter where the CAM device is most sensitive. Finally, it is not clear whether Rodgers' filter may be slid out far enough to allow for a hand-held radiation detector to be brought near the filter.

Accordingly, there is substantial room for improvement within the art.

OBJECTS OF THE INVENTION

It is an object of the invention to provide a sampling box that has a removable/replaceable filter cartridge in which the filter is placed in an isolated testing chamber.

It is a further object of the invention to provide a sampling box in which the replaceable filter cartridge is of extremely simple configuration.

It is yet a further object of the invention to provide a sampling box having a separate filter hold-down.

It is still yet a further object of the invention to provide a sampling box in which a maximum amount of radioactive particles are deposited on (in) the center of the filter.

It is still yet a further object of the invention to provide a sampling box that can be provided with or without CAM capability.

It is still yet a further object of the invention to provide a sampling box in which a precise fit between components to assure the unit remains sealed is unnecessary.

It is still yet a further object of the invention to provide a sampling box that has a higher efficiency than prior art sampling boxes.

These and other objects of the invention are achieved by a sampling box comprising: an upper body portion, the upper body having a single sample inlet, a testing chamber, and a bottom wall, the sample inlet in fluid communication with the testing chamber; a lower body portion, the lower body portion having a rectangular slot therethrough, a piston chamber, and a vacuum connection; a slidable drawer positioned within the rectangular slot, the drawer having a circular hole therein, the drawer further having an operative and an inoperative position; a filter cartridge, the filter cartridge movably fitted within the circular hole and supporting a filter; a movable piston located within the piston chamber and under the filter cartridge, the piston having a central passage through which a vacuum tube passes, the vacuum tube being in fluidic contact with the vacuum connection; a piston raising and lowering mechanism; whereby when the piston is raised it causes the filter cartridge to be raised against the bottom wall of the upper body portion such that all air entering said testing chamber through said sample inlet must pass through said filter and then exit said lower body portion through said vacuum connection via said vacuum tube.

BRIEF DESCRIPTION OF THE DRAWINGS

FIG. 6 is a sectional perspective view of a sampling box according to the invention.

DETAILED DESCRIPTION OF THE INVENTION

Figure 1:
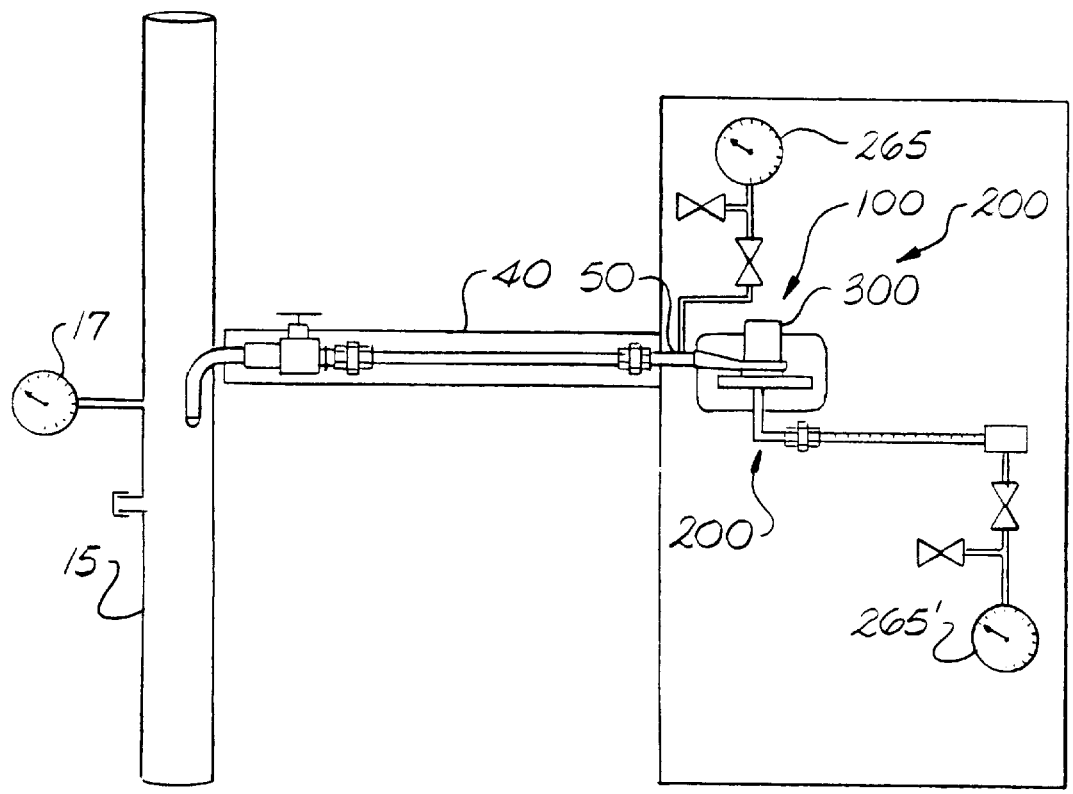
FIG. 1 is a schematic view of a typical application for a sampling box according to the invention.

With reference to the above drawings, a sampling box that meets and achieves the various objects of the invention set forth above will now be described.

As shown in FIGS. 1, 4–6, sampling box 100 according to the invention is placed between and in fluidic contact with sampling line 40 and vacuum line 200. Vacuum line 200, through piston 120 (having its outer circumference chrome plated for lubrication purposes) and vacuum tubing 125, draws sampled air from waste storage ventilation stack 15, having velocity gauge 17, through line 40 and into tapered inlet 50, through sampling box 100, and then out vacuum line 200. Inlet 50 is tapered by about 30° to better direct the air and particulate matter entrained therein towards the center of filter within sampling box 100. That is, the particles will be substantially slowed in the horizontal direction due to the taper and then deposit themselves onto the filter paper near its center. This is critical as the most sensitive point of the optional CAM to be described later is at its center. Any particulate matter entrained within the sampled air stream will be entrapped within the filter of the sampling box 100, as will be described below. While this taper substantially slows and directs the particulate matter, it does not do it abruptly as with 90° bends such as found in Rodgers, and which reduce the overall sampling box efficiency. Thus, while we achieve an efficiency in the range of 92% with 10 micrometer particles, Rodgers, as described above, only achieves an efficient of about 80%. With particles smaller than 10 micrometers, the instant device produces even higher efficiency ratings.

Figure 2A:
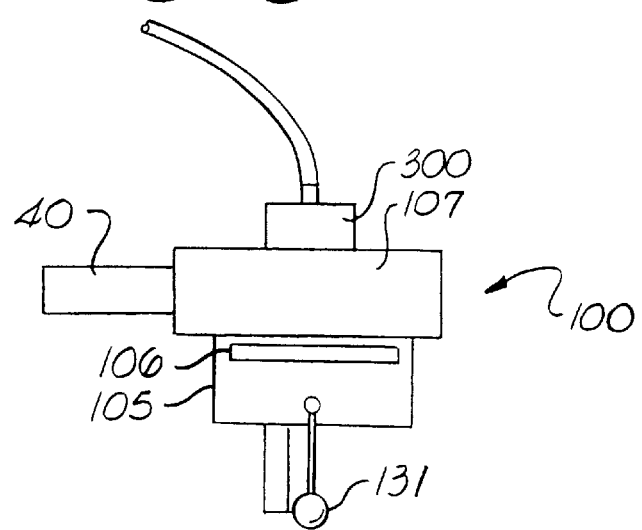
FIG. 2A is an elevation view of a sampling box according to the invention showing the positioning of the filter drawer.
Figure 2B:
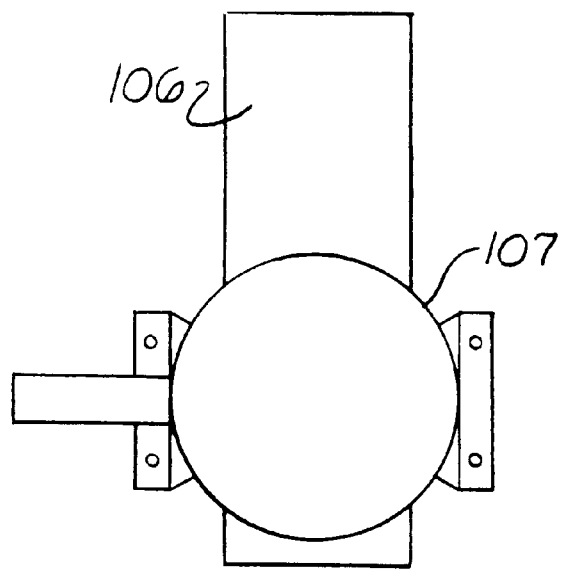
FIGS. 2B and 2C show plan views of a sampling box according to the invention in which the filter drawer is in its closed and open positions respectively.
Figure 2C:
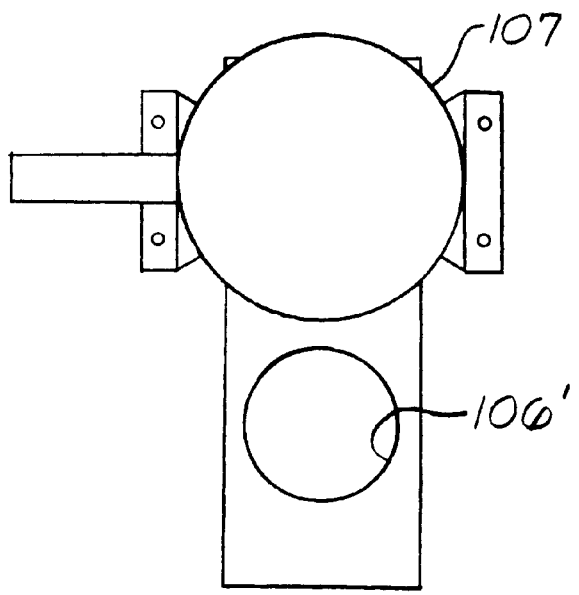

As shown in FIGS. 2A–C, sampling box 100 has lower body portion 105 and upper body potion 107, both of which will be made from stainless steel. Lower body portion 105 has a rectangular cut-out therethrough. Drawer 106 is placed into this cut-out. Drawer 106 will typically be made of brass because brass eliminates the need for lubrication of any brass-stainless steel interfaces. Furthermore, stainless steel and brass are resistant to vacuum distortion. The tolerances and precise fit between drawer 106 and lower body portion 105 are not critical for reasons described below. Finally, drawer 106 has circular cut-out 106' in one side thereof. When drawer 106 is in its operative position (FIG. 2B), circular cut-out 106', and therefore filter holder 112 that will be installed therein, are in line with inlet line 40 and vacuum line 200, inside of sampling box 100. When drawer 106 is in its inoperative position (FIG. 2C), circular cut-out 106' is positioned outside of sampling box 100 for the replacement and/or analysis of the filter, as will be described below. By this sliding structure, drawer 106 can be made integral with lower portion 105, i.e., non-removable therefrom, if the user so desires. In Rodgers, the drawer needed to be removed much further to change a filter cartridge. This is not as efficient as with the instant invention.

Figure 3A:
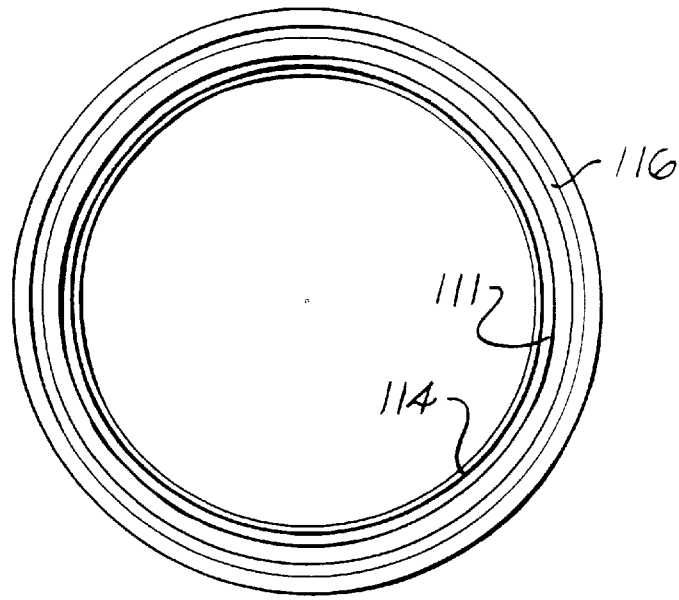
FIGS. 3A, 3B, and 3C show different views of the filter holder for use with the sampling box according to the invention.
Figure 3B:
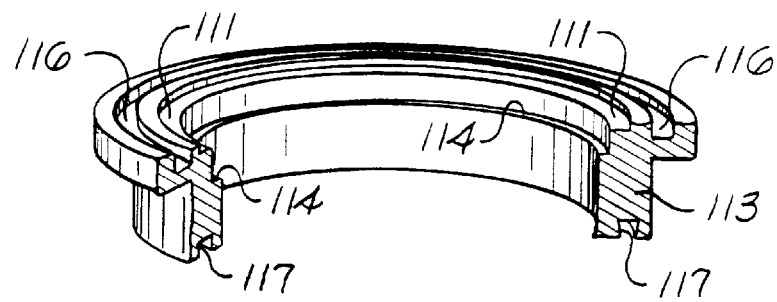
Figure 3C:
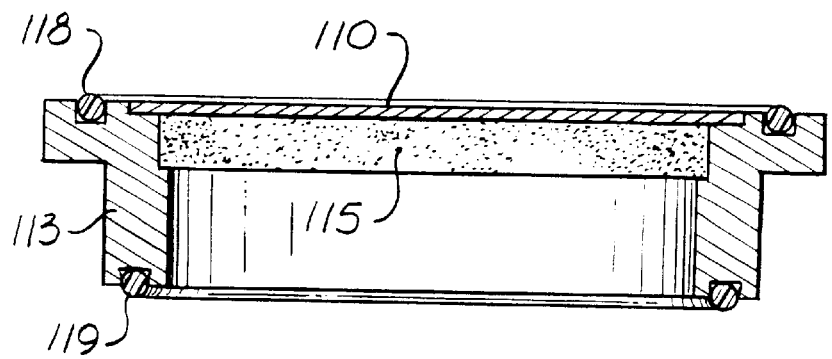

The details of filter holder 112 are shown in FIGS. 3A–C. Filter holder 112 comprises a unitary stainless steel annular ring 113. Ring 113 has various cut-outs and ledges therein. Cut-outs 116 (upper) and 117 (lower) are for receiving upper 118 and lower 119 O-rings, respectively in such a manner that they cannot be accidentally removed. Filter support grid ledge 114 receives filter support grid 115 made of sintered metal and which itself supports a standard 76 mm (diameter) filter 110, which is received in filter ledge 111. Thus, it can be seen that by use of filter holder 112, O-rings 118, 119 and filter 110 can be readily changed by anyone, without the use of tools, by the mere replacement of the old filter 110 with a new filter 110 or, if necessary, replacement of the old filter holder 112 with another preassembled filter holder 112 containing new O-rings 118, 119 and filter 110. The latter will usually only be necessary when there is a need to replace the O-rings. The used filter 110 can then be kept as a sample of record as per Environmental Protection Agency requirements.

Figure 4:
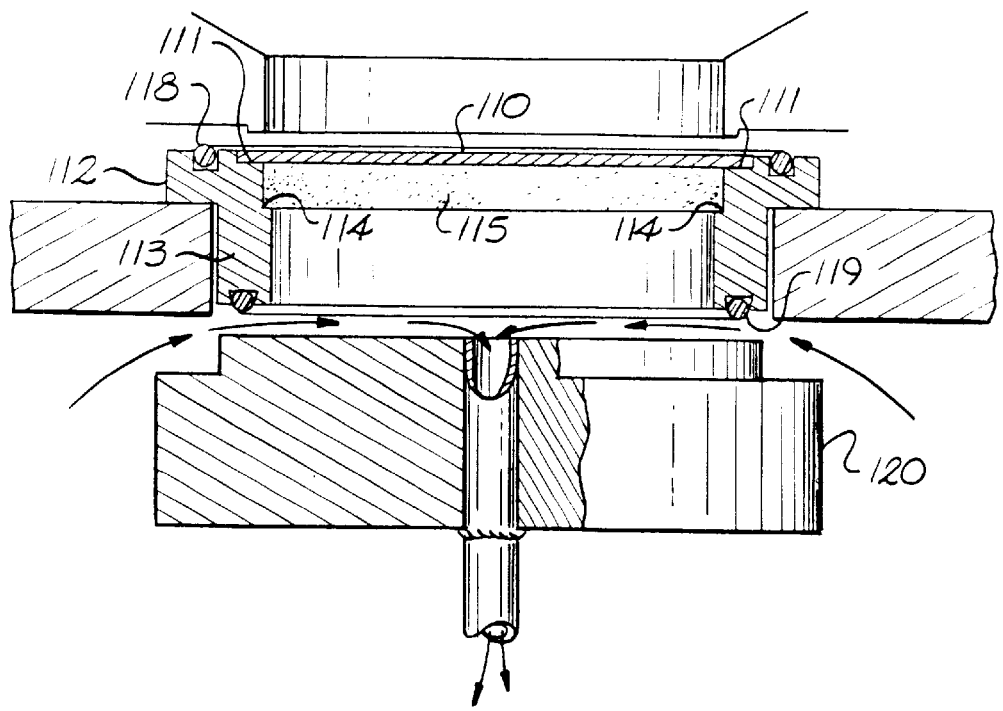
FIG. 4 is a sectional elevation view showing the details of the filter holder/drawer/piston interface in the sampling box according to the invention when the piston is in the inoperative position.
Figure 5:
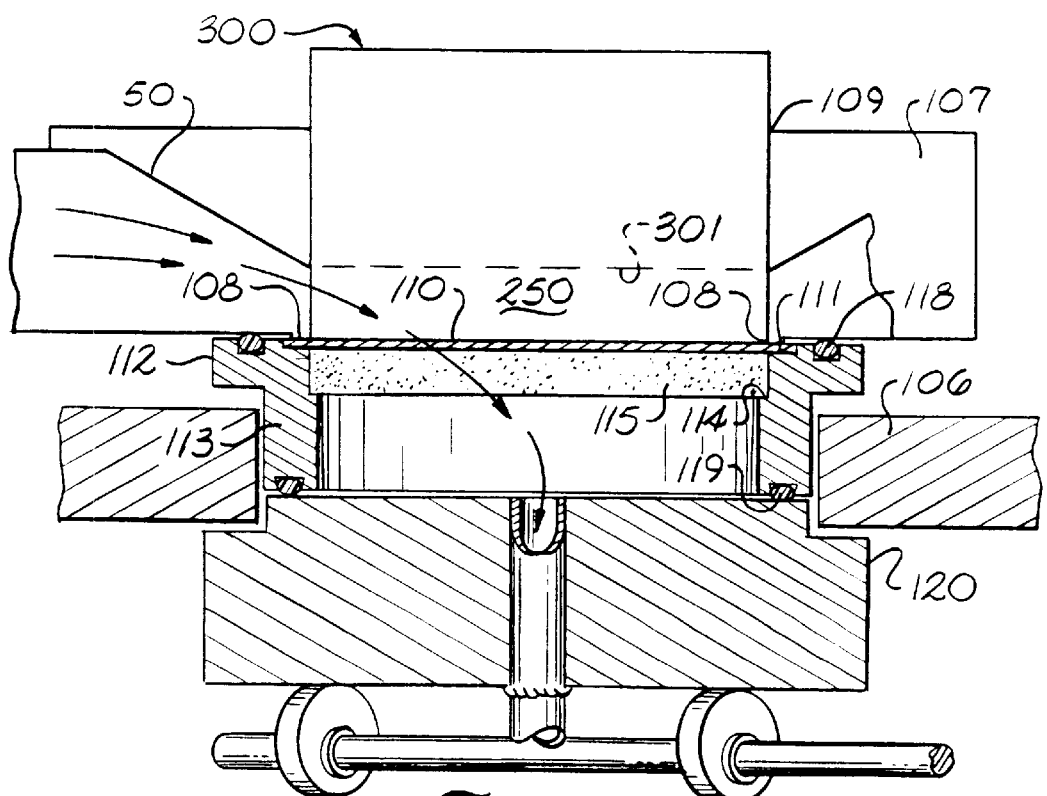
FIG. 5 is a more detailed sectional elevation view showing the filter holder/drawer/piston interface in the sampling box according to the invention when the piston is in the operative position.

With reference to FIGS. 4 and 5, a description of how filter holder 112 is changed will now be made. After an operator drops a complete filter holder 112 into drawer cut-out 106 and closes drawer 106, as shown in FIG. 4, filter holder 112 hangs within drawer 106 leaving various spaces through which sampled, potentially radioactive, air may escape. It is not critical for unit sealing purposes that the smaller outside diameter of filter holder 112 be almost identical to the diameter of hole 106' for reasons to be discussed below. The operator turns handle 131, which is attached to rod 132 having eccentric cams 133 thereon (FIG. 6). Eccentric cams 133 lift piston 120 into contact with lower O-ring 119. If drawer 106 is not fully closed it will be impossible to lift piston 120, thereby indicating that sampling box 100 is not ready for operation. This provides a safety check. However, when piston 120 can be lifted, it then lifts filter holder 112 until upper O-ring 118 is in contact with the bottom of upper body portion 107 and filter holder 112 is compressed between piston 120 and the bottom of upper body portion 107. This seals off the passage between inlet 40 and vacuum tubing 125 so that no entrained air can leave testing chamber 250 or contaminating air can enter testing chamber 250.

To detect leaks from testing chamber 250, a vacuum gauge, in one of two positions is used. The gauge may be positioned either before (gauge 265) or after (gauge 265') testing chamber 250. While it is preferred that gauge 265 be used because it is much more sensitive to changes in vacuum pressure, either gauge may be used. Thus, if either of gauges 265, 265' detect an abnormal value, an alarm will issue indicating a problem to the operator.

Additionally, the use of o-rings makes it such that the top and bottom surfaces of filter holder 112 need not be machined with high precision such as in Rodgers, where there needs to be a precise fit between components. Therefore, the instant filter holder 112 is much easier to manufacture. Further, because O-rings 118 and 119 are subject only to compression, not to any lateral motion such as scraping or twisting. The configuration of the O-rings 118 and 119 make it such that they are subject to less wear, thus, obviating the need for lubrication. Finally, the bottom of upper body 107 has interferences 108 which come directly into contact with filter 110, holding down and sandwiching filter 110 in its proper position (FIG. 5). As can be seen in FIG. 5, when in the operative position, there are no extraneous portions of filter holder 112 in the flow stream, thus, eliminating the possibility of contamination by an operator engaging holder 112 at its outermost circumference. Therefore, filter holder 112 cannot be contaminated and may be removed from drawer 106 with minimum risk. Similarly, when piston 120 is lowered by turning handle 131 in the opposite direction, it automatically breaks the vacuum contained within chamber 245 and therefore eliminates the need for additional valving.

To provide for the potentiality that sampling box 100 can be used in a continuous real time monitoring (CAM) environment, upper body portion 107 has a circular cut-out or aperture 109 therein. In the preferred embodiment, circular cut-out 109 receives a radiation detector 300, such as, but not limited to, a conventional GM tube positioned 0.5 inches above and parallel to filter 110, for providing continuous real time monitoring (CAM) of the quantity of radioactive materials collected by filter 110. Because the sensitive face 301 of radiation detector 300 is not exposed when filter 110 is changed, radiation detector 300 is better protected from physical damage and will, thus, have an extended operable life. Furthermore, radiation detector 300 is centered over filter 110. This is important because face 301 is most sensitive at its center and with the instant invention the radioactive particles are more readily deposited in the,center of filter 110 due to the 30° taper of inlet 50.

Circular cut-out 109 also allows for the easy replacement of radiation detectors should they become inoperative.

When CAM sampling is not required, circular cut-out 109 can be filled by a metallic slug (not shown). This increased flexibility is lacking in devices that are strictly CAM or not-CAM. For example, while Rodgers may be used in non-CAM applications by shutting off his radiation detector, the purchaser of Rodgers is still paying for the incorporation of the detector into the overall sampling apparatus. However, with the instant invention, the purchaser only pays for the CAM components if the purchaser will actually be using CAM.

The above description is given in reference to a sampling box. However, it is understood that many variations are apparent to one of ordinary skill in the art from a reading of the above specification and such variations are within the spirit and scope of the instant invention as defined by the following appended claims.

That which is claimed:

1. A sampling box, comprising:

an upper body portion, said upper body having a single substantially straight sample inlet having a receiving end and a discharge end, a testing chamber, and a bottom wall, said sample inlet tapered from a first dimension at said receiving end to a second dimension smaller than said first dimension at said discharge end such that air and particulate matter entrained therein are directed towards a center of a filter, said sample inlet in fluid communication with said testing chamber;

a lower body portion, said lower body portion having a rectangular slot therethrough, a piston chamber, and a vacuum connection;

a slidable drawer positioned within said rectangular slot, said drawer having a circular hole therein, said drawer further having an operative and an inoperative position;

a filter cartridge, said filter cartridge movably fitted within said circular hole and supporting said filter;

a movable piston located within said piston chamber and under said filter cartridge, said piston having a central passage through which a vacuum tube passes, said vacuum tube being in fluid contact with said vacuum connection;

a piston raising and lowering mechanism;

whereby when said piston is raised it causes said filter cartridge to be raised against said bottom wall of said upper body portion such that all air entering said testing chamber through said sample inlet must pass through said filter and then exit said lower body portion through said vacuum connection via said vacuum tube.

2. The sampling box according to claim 1, wherein said filter cartridge comprises:

an annular ring having first and second annular ledges;

a filter support received in said first annular ledge;

a filter received in said second ledge;

first and second O-rings located in grooves in top and bottom surfaces of said annular ring, respectively;

such that when in the raised position, said second O-ring is in contact with said piston and said first O-ring is in contact with said bottom wall of said upper body portion.

3. The sampling box according to claim 2, wherein said testing chamber further comprise downwardly directed interferences and when said piston is in the raised position, said filter is sandwiched between said filter support and said interference.

4. The sampling box according to claim 2, wherein said filter support comprises a grid.

5. The sampling box according to claim 1, wherein said sample inlet tapered interior causes particulate material entrained within air flowing through said sampling box to be substantially slowed down in the area of a center of said filter cartridge.

6. The sampling box according to claim 5, wherein said sample inlet has a top wall having a downward slope.

7. The sampling box according to claim 6, wherein said downward slope is 30°.

8. The sampling box according to claim 1, further comprising a vacuum gauge for determining if there is a leak in said testing chamber.

9. The sampling box according to claim 1, wherein when said piston is lowered the vacuum is broken without the use of additional valving.

\* \* \* \* \*